US007028554B2

(12) United States Patent
Adamchuk et al.

(10) Patent No.: US 7,028,554 B2
(45) Date of Patent: Apr. 18, 2006

(54) INSTRUMENTED DEEP TILLAGE IMPLEMENT

(75) Inventors: Viacheslav Ivanovych Adamchuk, Lincoln, NE (US); Andrey Valeryevich Skotnikov, Cedar Falls, IA (US); Justin Douglas Speichinger, Malmo, NE (US)

(73) Assignee: Deere & Company, Moline, IL (US)

( * ) Notice: Subject to any disclaimer, the term of this patent is extended or adjusted under 35 U.S.C. 154(b) by 0 days.

(21) Appl. No.: 10/617,614

(22) Filed: Jul. 11, 2003

(65) Prior Publication Data

US 2005/0005704 A1   Jan. 13, 2005

(51) Int. Cl.
*G01B 5/00* (2006.01)
*G01B 7/16* (2006.01)
*G01L 1/00* (2006.01)
*G01N 3/00* (2006.01)
*G01N 33/24* (2006.01)

(52) U.S. Cl. ...................................................... 73/784
(58) Field of Classification Search ................. 73/784, 73/84, 818, 866, 9, 718; 111/200; 172/700
See application file for complete search history.

(56) References Cited

U.S. PATENT DOCUMENTS

| 4,554,819 | A | * | 11/1985 | Ali .................................. 73/9 |
| 4,579,003 | A | * | 4/1986 | Riley ........................... 73/784 |
| 5,524,560 | A | | 6/1996 | Carter ......................... 111/200 |
| 5,726,349 | A | | 3/1998 | Palmertree et al. ............. 73/84 |
| 5,964,300 | A | * | 10/1999 | Wattonville et al. ......... 172/700 |
| 6,041,582 | A | | 3/2000 | Tiede et al. ................... 56/10.2 |
| 6,062,090 | A | * | 5/2000 | Bachhuber et al. ........... 73/784 |
| 6,217,260 | B1 | * | 4/2001 | He .............................. 405/237 |
| 6,389,999 | B1 | * | 5/2002 | Duello ........................ 111/200 |
| 6,647,799 | B1 | * | 11/2003 | Raper et al. .................. 73/784 |
| 6,701,857 | B1 | * | 3/2004 | Jensen et al. ................ 111/200 |
| 6,834,550 | B1 | * | 12/2004 | Upadhyaya et al. ........... 73/784 |
| 2003/0009286 | A1 | | 1/2003 | Shibusawa et al. ............. 702/2 |
| 2003/0066357 | A1 | | 4/2003 | Upadhyaya et al. ........... 73/818 |

OTHER PUBLICATIONS

No Author, American Society of Agricultural Engineers, ASAE EP542 Feb. 1999, Procedures for Using and Reporting Data Obtained with the Soil Cone Penetrometer.
No Author, American Society of Agricultural Engineers, ASAE S313.3 Feb. 2004, Soil Cone Penetrometer.

* cited by examiner

*Primary Examiner*—Max Noori
*Assistant Examiner*—Octavia Davis

(57) ABSTRACT

An instrument and method for variable depth tillage is provided. A soil engaging implement has a pair of load cells and at least one strain gauge set mounted thereon. The load cells are used to determine a linear trend of topsoil resistance pressure change with depth as the soil engaging implement is drawn through the soil. The strain gauges are used to measure torque on the soil engaging implement caused by the load transmitted through the at least two load cells as well as the load applied to the point of the soil engaging implement. The linear trend of topsoil resistance pressure change with depth and the torque on the soil engaging implement are then used to determine both measured and predicted mechanical soil resistance to penetration applied to the point and the difference between the two values serves as an input for tillage depth adjustment.

9 Claims, 1 Drawing Sheet

INSTRUMENTED DEEP TILLAGE IMPLEMENT

FIELD OF THE INVENTION

The present invention relates generally to precision farming implements and methods. More particularly, the present invention relates to an apparatus and method for determining, evaluating and analyzing soil profile mechanical resistance measurements. Specifically, the present invention relates to such an apparatus and method wherein an instrumented deep tillage implement is used to make such evaluations in real time.

BACKGROUND OF THE INVENTION

In recent years the economics of farming have made efficient farm management critical. Soil erosion and chemical runoff have led farmers to adopt various precision farming techniques, including conservation tillage. Further soil characteristics and environmental conditions have a direct impact on crop yield. Specifically, soil compaction can have a direct negative effect on crop yields. Regions of high mechanical resistance in the soil may arise as natural soil features, be caused by heavy farm machinery or by the formation of plow pans. Compacted soils with high strength reduce growth rates of crop roots and thus limit the acquisition of water and nutrients to the plant. This may affect crop yield. Different soil tillage practices are thus implemented to reduce soil compaction.

Advances in site-specific crop management (precision agriculture) provide capabilities to vary soil treatment across an agricultural field. Soil tillage is one of them. Although, conventional methods of crop management provide similar impact across the entire field, different parent material, topography and past management can cause significant variability of soil compaction. Therefore, local (spot) or variable depth tillage may increase efficiency of this field operation. By avoiding tillage of soil with a relatively low level of compaction, both economical and environmental improvements of crop production can be achieved through: 1) reduction of energy waste, and 2) preserving developed soil structure.

Soil compaction is related to several physical and mechanical characteristics and is defined specifically as the volume change produced by momentary load application caused by rolling, tamping or vibration. Measurement of mechanical resistance of soil to a penetrating object is recognized as a conventional method to estimate soil strength at a given point. The American Society of Agricultural Engineers have specified a penetrometer with a conical tip as the standard method to determine a soil strength index from a static penetration test.

Even if automated, cone penetrometer measurements are time consuming and highly variable. On-the-go measurements of soil mechanical resistance, however, allow for a substantial increase in measurement density. A number of prototype systems have been developed to map soil mechanical resistance on-the-go. Some have been used to determine horizontal soil resistance at a particular depth; others have been developed to quantify different operation parameters associated with implement draft performance. These systems allow mapping spatial variability of soil resistance; however, multiple depth measurements are needed to prescribe variable depth tillage. Other prototype systems have been developed to determine both spatial and depth variation of soil resistance or use an instrumented subsoiler to map "hard-pans" through a dynamic operation of the implement. The resulting maps could be used to prescribe variable depth tillage in different field areas. A control system can then be used to guide tillage equipment at appropriate depth.

Accordingly, there is a clear need in the art for an instrumentation system based on a commercial implement for deep soil tillage that can identify changes of soil mechanical resistance with depth and guide itself to appropriate operation depth in real-time.

SUMMARY OF THE INVENTION

In view of the foregoing, it is an object of the invention to provide a means for monitoring changes in soil mechanical resistance using instrumentation based on a commercial implement.

Another object of the invention is the provision of such a means which can monitor soil mechanical resistance at various depths in real time.

A further object of the invention is to provide such a means which can utilize soil mechanical resistance measurements to guide itself to appropriate tillage depths in real time.

An additional object of the invention is the provision of such a means which is compatible with existing commercially available agricultural equipment.

The foregoing and other objects of the invention together with the advantages thereof over the known art which will become apparent from the detailed specification which follows are attained by an instrumentation system for variable depth tillage comprising: at least one soil engaging implement; at least two load cells mounted to the soil engaging implement; and, at least one set of strain gauges mounted to the soil engaging implement.

Other objects of the invention are attained by a method for determining tillage depth for a soil engaging implement comprising the steps of: providing at least one soil engaging implement having an upper end mounted to a support structure, a lower end, a point for engaging the soil mounted to the lower end, a leading edge, and a protective shin mounted to the leading edge; interposing at least two load cells between the protective shin and the leading edge of the soil engaging implement; mounting at least one set of strain gauges on the soil engaging implement; determining a linear trend of topsoil resistance pressure change with depth from the load cells as the soil engaging implement is drawn through the soil; determining from the strain gauges a measured torque on the soil engaging implement caused by the load transmitted through the at least two load cells as well as the load applied to the point of the soil engaging implement; determining measured ($p_p$) and predicted ($p_{sh}$) mechanical soil resistance to penetration applied to the point from the linear trend of topsoil resistance pressure change with depth and the torque on the soil engaging implement; using the difference between measured and predicted mechanical soil resistance to penetration applied to the point as an input for adjusting the depth of the soil engaging implement.

In general, an instrument and method for variable depth tillage is provided. A soil engaging implement has a pair of load cells and at least one strain gauge set mounted thereon. The load cells are used to determine a linear trend of topsoil resistance pressure change with depth as the soil engaging implement is drawn through the soil. The strain gauges are used to measure torque on the soil engaging implement caused by the load transmitted through the load cells as well as the load applied to the point of the soil engaging implement. The linear trend of topsoil resistance pressure change with depth and the torque on the soil engaging implement are then used to determine both measured and predicted mechanical soil resistance to penetration applied to the point and the difference between the two values serves as an input for tillage depth adjustment.

To acquaint persons skilled in the art most closely related to the present invention, one preferred embodiment of the invention that illustrates the best mode now contemplated for putting the invention into practice is described herein by and with reference to, the annexed drawings that form a part of the specification. The exemplary embodiment is described in detail without attempting to show all of the various forms and modifications in which the invention might be embodied. As such, the embodiment shown and described herein is illustrative, and as will become apparent to those skilled in the art, can be modified in numerous ways within the spirit and scope of the invention—the invention being measured by the appended claims and not by the details of the specification.

BRIEF DESCRIPTION OF THE DRAWINGS

For a complete understanding of the objects, techniques, and structure of the invention reference should be made to the following detailed description and accompanying drawings, wherein.

DESCRIPTION OF THE PREFERRED EMBODIMENT

Figure 1:
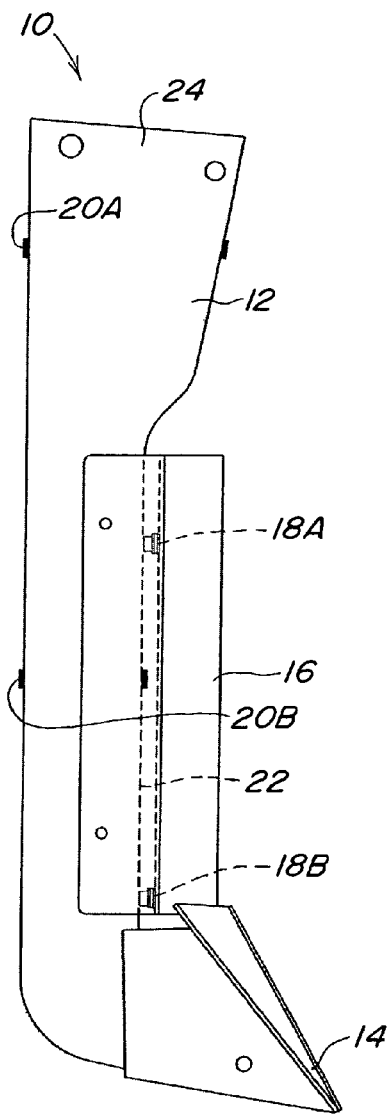
FIG. 1 is an elevational view of a soil engaging implement according to the invention.

With reference now to the drawings it can be seen that an instrumentation system for variable depth tillage is designated generally by the numeral 10. A commercially available straight standard 12 is used to house the instrumentation system. A point 14 and protective shin 16 are provided to protect installed transducers. The instrumentation system further includes two washer type load cells 18A and 18B, and two sets of strain gauges 20A and 20B preferably configured in a Wheatstone full bridge type I. Both load cells 18 are installed on the inner surface 22 of the protective shin 16 and carry the entire load applied to the shin 16 while tilling. One set of strain gauges 20A is preferably attached to the standard 12 between the two load cells 18, and the other set 20B is preferably installed right below the mounting portion 24 of the standard 12.

The load cells 18 are used to determine a linear trend (gradient) of topsoil resistance pressure change with depth. The strain gauges 20, on the other hand, measure torque caused by the load transmitted through the load cell(s) 18 as well as by the load applied to the point 14. Therefore, it is possible to determine both measured and predicted mechanical soil resistance to penetration applied to the point 14. The difference between these two values serve as a key input for the tillage depth adjustment.

An interface is used to acquire the signal (conditioned with a signal-conditioning accessory) obtained from a 12-bit A/D converter. All measurements are preferably performed with 1 Hz frequency (averages with actual sampling at approximately 120 Hz) and stored in a text delimited file.

Known gauge factors and excitation voltages are used to calculate strain measured by each set of strain gauges 20. The load cells 18 are calibrated using a pre-calibrated load cell with forces of up to 10 kN. Every transducer except the depth sensor (not shown) is set to 0 when no load is applied.

An ultrasonic distance sensor (not shown) is used to measure tillage depth. Operation depths typically ranges from 0 to 60 cm. If mapping capabilities are required, geographic position (longitude and latitude) as well as true travel speed can be determined with a GPS (Global Positioning System) receiver (not shown).

Figure 3:
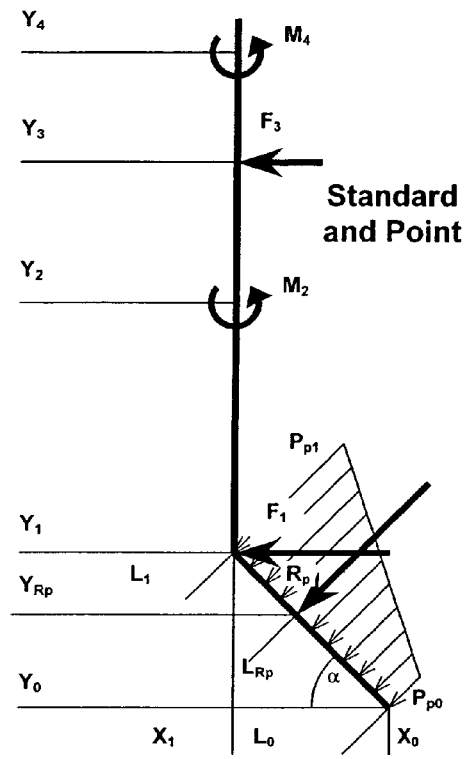
Figure 2:
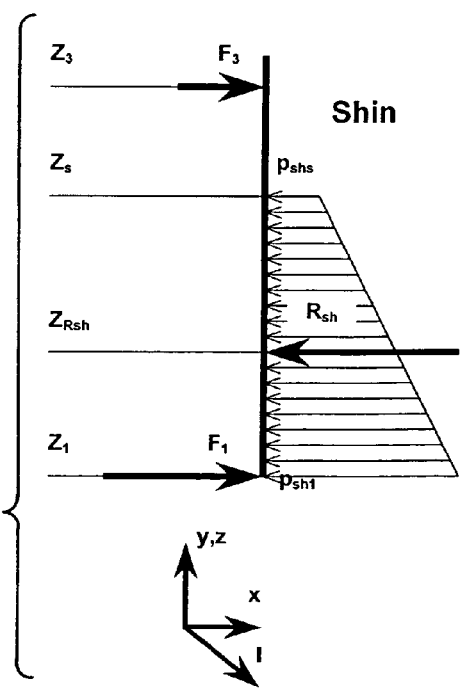
FIG. 2 is a free body diagram of the shin of the implement according to the invention; and, FIG. 3 is a free body diagram of the standard and point assembly of the implement according to the invention.

Free body diagrams of both the shin 16 and the standard-point 12, 14, assembly are shown in FIGS. 2 & 3. The diagrams assume that the front edge of the shin penetrates the soil perpendicularly to the surface. Load cell 18A is installed at the top of the point depth. Soil resistance applied to the shin 16 is represented by a linear distribution of soil resistance pressure $p_{sh}$. The distance between soil surface and load cell 18A is variable and depends on tillage depth. Similarly, soil resistance applied to the point 14 is represented by linear distribution $p_p$. Since both distributions can be characterized by two parameters, a total of four measurements is required. The free body diagram of the shin 16 shown in FIG. 2 is used to derive $p_{sh}=f(y)$, where y is a vertical coordinate with respect to the tip of the point 14. Similarly, z is a vertical coordinate with respect to load cell 18A (top of the point 14). The magnitude and position of resultant resistance force ($R_{sh}$) can be defined as:

$$R_{sh}=F_1+F_3 \qquad (1)$$

$$Z_{Rsh} = \frac{F_3 Z_3}{R_{sh}} \qquad (2)$$

where
$R_{sh}$=Total resistance force acting on the shin 14, N
$F_1$=Load cell 18A measurement, N
$F_3$=Load cell 18B measurement, N
$Z_{Rsh}$=z coordinate of the resultant force $R_{sh}$, mm
$Z_3$=z coordinate of load cell 18B, mm Both $R_{sh}$ and $Z_{Rsh}$ can be used to define two values of linear pressure distribution:

$$p_{shs} = \frac{2R_{sh}}{b_{sh}Z_s}\left(3\frac{Z_{Rsh}}{Z_s} - 1\right) \qquad (3)$$

$$p_{shl} = \frac{2R_{sh}}{b_{sh}Z_s}\left(2 - 3\frac{Z_{Rsh}}{Z_s}\right) \qquad (4)$$

where
$p_{shs}$=predicted value of soil resistance pressure at soil surface, MPa
$p_{sh1}$=predicted value of soil resistance pressure at load cell 18A, MPa
$b_{sh}$=frontal width of the shin 14, mm
$Z_s$=z coordinate of soil surface, mm Since $y=z+Y_1$, $p_{sh}=f(y)$ can be defined as:

$$p_{sh}(y) = p_{shl} + \frac{p_{shs} - p_{shl}}{Y_s - Y_1}(y - Y_1) \qquad (5)$$

where $Y_1$=y coordinate of load cell 18A, mm $Y_3$=y coordinate of load cell 18B, mm Similarly, a free body diagram of the standard 12 and point 14 assembly is shown in FIG. 3 and is used to derive $p_p$=f(y). However, two new coordinates x and l are added. Coordinate x represents horizontal distance with respect to the front of the shin 16. Coordinate l represents the distance along front surface of the point 14 with respect to its upper end (l=0 if both x=0 and z=0).

Both sets of strain gauges 20 are used to calculate bending moment (torque) at the corresponding cross-sections:

$$M_2 = \frac{1}{6} E b_{st} h_2^2 \varepsilon_2 \cdot 10^{-6} \quad (6)$$

$$M_4 = \frac{1}{6} E b_{st} h_4^2 \varepsilon_4 \cdot 10^{-6} \quad (7)$$

where $M_2$ and $M_4$=bending moment at strain gauges 20A and 20B respectively, N·mm E=modulus of elasticity (207 GPa for steel)

$b_{st}$=frontal width of the standard, mm $h_2$ and $h_4$=cross-section length of the standard at strain gauges 20A and 20B respectively, mm $\varepsilon_2$ and $\varepsilon_4$=strain measured by strain gauge bridges 20A and 20B respectively, μm/m The magnitude and location of the resultant resistance force $R_p$ can be defined as:

$$R_p = \frac{A_2 - A_4}{B_2 - B_4} \quad (8)$$

$$L_{Rp} = \frac{A_4 B_2 - A_2 B_4}{A_2 - A_4} \quad (9)$$

where $R_p$=Total resistance force acting on the point 14, N $L_{Rp}$=l coordinate of the resultant force $R_p$, mm $A_2$, $A_4$=momentum of force $R_p$ sensed by strain gauges 20A and 20B, N·mm $B_2$, $B_4$=geometry parameters, mm $$A_2 = M_2 - F_1 Z_2 \quad (10)$$

$$B_2 = Z_2 \sin \alpha + X_2 \cos \alpha \quad (11)$$

$$A_4 = M_4 - F_1 Z_4 - F_3 (Z_4 - Z_3) \quad (12)$$

$$B_4 = Z_4 \sin \alpha + X_4 \cos \alpha \quad (13)$$

where $Z_1$, $Z_2$, $Z_3$, $Z_4$=z coordinates of corresponding transducers, mm $X_2$, $X_4$=absolute values of x coordinates for cross-sections center at gauges 20A and 20B respectively, mm α=slope of the point 14:

$$\tan \alpha = \frac{Y_1}{X_0} \quad (14)$$

Both $R_p$ and $L_{Rp}$ can be used to define two values of the linear pressure distribution:

$$p_{p0} = \frac{2 R_p}{b_p L_0} \left( 3 \frac{Z_{Rp}}{L_0} - 1 \right) \quad (15)$$

$$p_{p1} = \frac{2 R_p}{b_p L_0} \left( 2 - 3 \frac{L_{Rp}}{L_0} \right) \quad (16)$$

where $L_0$=the total length of front the point 14, mm $b_p$=frontal width of the point 14, mm Using these parameters, $p_p$=f(y) can be defined as:

$$p_p(y) = p_{p0} + \frac{p_{p1} - p_{p0}}{Y_1} y \quad (17)$$

To compare both predicted $p_{sh}$ and estimated $p_p$ resistance pressure applied to the point 14, $y=Y_{Rp}$ coordinate can be used:

$$Y_{Rp} = Y_1 - L_{Rp} \sin \alpha \quad (18)$$

Although, defining both distributions $p_{sh}$ and $p_p$ is feasible using four transducers, inaccurate measurements can significantly change slopes of both distributions. Therefore, two simplifications are used for practical applications:

1. Set $p_{shs}$ to 0 assuming no mechanical resistance at the surface. In this case, Equation 4 can be substituted with:

$$p_{sh1} = \frac{2 R_{sh}}{b_{sh}(Y_s - Y_1)} \quad (19)$$

2. Assume $p_{p0}$ equal to $p_{p1}$ and define $R_p$ using averages from two sets of strain gauges:

$$R_p = \frac{1}{2}\left( \frac{A_2}{L_{Rp} + B_2} + \frac{A_4}{L_{Rp} + B_4} \right) \quad (20)$$

If only one set of strain gauges is used, Equation 20 can be simplified to $R_p = A(L_{rp} + B)$, where A and B are defined for the existing set of strain gauges only. In this case, $L_{Rp} = L_0/2$, and Equations 15 and 16 can be combined in:

$$p_{p0} = p_{p1} = \frac{R_p}{b_p L_0} \quad (21)$$

Those skilled in the art will recognize that the equations set forth above can be incorporated into an appropriate algorithm for automatically controlling the depth of a soil engaging implement during conventional tillage operations. Thus the soil engaging implement can be raised or lowered in real time so as to obtain optimal tillage depth based upon soil characteristics.

Thus it can be seen that the objects of the invention have been satisfied by the structure presented above. While in accordance with the patent statutes, only the best mode and preferred embodiment of the invention has been presented and described in detail, it is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly and legally entitled.

What is claimed is:

1. An instrumentation system for variable depth tillage comprising:
    at least one soil engaging tillage implement;
    at least two load cells mounted to the soil engaging tillage implement; and,
    at least one set of strain gauges mounted to the soil engaging tillage implement wherein the load cells are used to determine a linear trend of topsoil resistance pressure change with depth as the soil engaging tillage implement is drawn through the soil and wherein the at least one set of strain gauges is used to measure torque on the soil engaging tillage implement caused by the load transmitted through the at least two load cells as well as the load applied to the point of the soil engaging tillage implement.

2. The instrumentation system for variable depth tillage as described in claim 1 wherein the soil engaging tillage implement has an upper end mounted to a support structure, a lower end, a point for engaging the soil mounted to the lower end, a leading edge, and a protective shin mounted to the leading edge.

3. The instrumentation system for variable depth tillage as described in claim 2 wherein the at least two load cells are interposed between the protective shin and the leading edge of the soil engaging tillage implement.

4. The instrumentation system for variable depth tillage as described in claim 1 wherein each set of strain gauges is a bridge type configuration.

5. The instrumentation system for variable depth tillage as described in claim 2 wherein two sets of strain gauges are mounted to the soil engaging tillage implement at different depths.

6. The instrumentation system for variable depth tillage as described in claim 1 wherein the linear trend of topsoil resistance pressure change with depth and the torque on the soil engaging tillage implement are used to determine measured ($p_p$) and predicted ($p_{sh}$) mechanical soil resistance to penetration applied to the point and the difference between the two values is an input for tillage depth adjustment.

7. The instrumentation system for variable depth tillage according to claim 6 wherein a linear distribution of soil resistance pressure $p_{sh}=f(y)$ is calculated from a free body diagram based on load cell and depth measurements where y is the vertical coordinate with respect to the tip of the point (14).

8. The instrumentation system for variable depth tillage according to claim 7 wherein a free body diagram of the standard and point assembly is used to derive $p_p=f(y)$ based on both load cell and strain gauge measurements and the difference between $p_p$ and $p_{sh}$ serves as a key input to guide the soil engaging tillage implement to an appropriate operation depth.

9. A method for determining tillage depth for a soil engaging implement comprising the steps of:
    providing at least one soil engaging tillage implement having an upper end mounted to a support structure, a lower end, a point for engaging the soil mounted to the lower end, a leading edge, and a protective shin mounted to the leading edge;
    interposing at least two load cells between the protective shin and the leading edge of the soil engaging tillage implement;
    mounting at least one set of strain gauges on the soil engaging tillage implement;
    determining a linear trend of topsoil resistance pressure change with depth from the load cells as the soil engaging tillage implement is drawn through the soil;
    determining from the strain gauges a measured torque on the soil engaging tillage implement caused by the load transmitted through the at least two load cells as well as the load applied to the point of the soil engaging tillage implement;
    determining measured ($p_p$) and predicted ($p_{sh}$) mechanical soil resistance to penetration applied to the point from the linear trend of topsoil resistance pressure change with depth and the torque on the soil engaging tillage implement;
    using the difference between measured and predicted mechanical soil resistance to penetration applied to the point as an input for adjusting the depth of the soil engaging tillage implement.

* * * * *